US009820988B2

(12) United States Patent
Engel et al.

(10) Patent No.: US 9,820,988 B2
(45) Date of Patent: Nov. 21, 2017

(54) TREATMENT OF EPILEPTIC DISORDERS IN FELINE ANIMALS

(71) Applicant: Boehringer Ingelheim Vetmedica GmbH, Ingelheim am Rhein (DE)

(72) Inventors: Odilo Randolf Engel, Ingelheim am Rhein (DE); Annalena Michel, Mainz (DE); Frerich De Vries, Ingelheim am Rhein (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 0 days.

(21) Appl. No.: 14/662,552

(22) Filed: Mar. 19, 2015

(65) Prior Publication Data

US 2015/0265624 A1 Sep. 24, 2015

(30) Foreign Application Priority Data

Mar. 24, 2014 (WO) .................. PCT/EP2014/055843
May 9, 2014 (WO) .................. PCT/EP2014/059525
Aug. 8, 2014 (EP) ..................................... 14180415

(51) Int. Cl.
*A61K 31/5377* (2006.01)
*A61K 31/515* (2006.01)

(52) U.S. Cl.
CPC ........ *A61K 31/5377* (2013.01); *A61K 31/515* (2013.01)

(58) Field of Classification Search
CPC .......................... A61K 31/5377; A61K 31/515
See application file for complete search history.

(56) References Cited

U.S. PATENT DOCUMENTS

| | | | |
|---|---|---|---|
| 3,932,452 | A | 1/1976 | Schwan et al. |
| 4,044,021 | A | 8/1977 | Hanifin, Jr. et al. |
| 5,869,481 | A | 2/1999 | Lankau et al. |
| 5,994,347 | A | 11/1999 | Rostock et al. |
| 7,932,273 | B2 | 4/2011 | Schmid et al. |
| 8,741,350 | B2 | 6/2014 | Folger et al. |
| 8,859,540 | B2 | 10/2014 | Rundfeldt et al. |
| 8,962,617 | B2 | 2/2015 | Rundfeldt et al. |
| 2005/0070537 | A1 | 3/2005 | Rundfeldt et al. |
| 2005/0234104 | A1 | 10/2005 | Schmid et al. |
| 2008/0027057 | A1 | 1/2008 | Rundfeldt et al. |
| 2013/0040937 | A1 | 2/2013 | Albrecht et al. |
| 2013/0065898 | A1 | 3/2013 | Rundfeldt et al. |
| 2014/0227351 | A1 | 8/2014 | Folger et al. |
| 2016/0367562 | A1 | 12/2016 | Rundfeldt et al. |

FOREIGN PATENT DOCUMENTS

| | | | |
|---|---|---|---|
| CA | 2184871 | C | 8/2001 |
| CA | 2476054 | A1 | 9/2003 |
| CN | 1638771 | A | 7/2005 |
| CN | 1845917 | A | 10/2006 |
| EP | 1074252 | A2 | 2/2001 |
| WO | 9709314 | A1 | 3/1997 |
| WO | 9900346 | A1 | 1/1999 |
| WO | 2004032938 | A1 | 4/2004 |
| WO | WO 2004/032938 | * | 4/2004 |
| WO | 2013024023 | A1 | 2/2013 |

OTHER PUBLICATIONS

Lane, "Medical management of recurrent seizures in dogs and cats", J Vet Intern Med. Jan.-Feb. 1990;4(1):26-39.*
"Epilepsy/Seizures". [Accessed at: http://www.neurologychannel.com/common/printpage.php on Jan. 1, 2007] pp. 1-2.
Bailey et al., "The Seizuring Cat Diagnostic work-up and therapy". Journal of Feline Medicine and Surgery, vol. 11, 2009, pp. 385-394.
Belzung et al., "Measuring normal and pathological anxiety-like behaviour in mice: a review". Behavioural Brain Research, vol. 125, 2001, pp. 141-149.
Berendt et al., "Epilepsy and Seizure Classification in 63 Dogs: A Reappraisal of Veterinary Epilepsy Terminology". Journal of Veterinary Internal Medicine, vol. 13, 1999, pp. 14-20.
Bialer et al., "Progress report on new antiepileptic drugs: a summary of the Fifth Eilat Conference (EILAT V)". Epilepsy Research, vol. 43, 2001, pp. 11-58.
Bialer et al., "Progress report on new antiepileptic drugs: a summary of the fourth Eilat conference (EILAT IV)". Epilepsy Research, vol. 34, 1999, pp. 1-41.
Chapman, Astrid G., "Therapeutic prospects for novel excitatory amino acid antagonists in idiopathic generalized epilepsy". Idiopathic Generalized Epilepsies: Clinical, Experimental and Genetic Aspects, John Libbey & Company Ltd., London, 1994, pp. 463-471.
Fernandez-Guasti et al., "Species differences in the mechanism through which the serotonergic agonists indorenate and ipsapirone produce their anxiolytic action". Psychopharmacology, vol. 107, 1992, pp. 61-68.
French, Jacqueline A., "The Role of New Antiepileptic Drugs". The American Journal of Managed Care, vol. 7, No. 7, Sup., Jul. 2001, pp. S209-S214.
Hogg, Sandy, "A Review of the Validity and Variability of the Elevated Plus-Maze as an Animal Model of Anxiety". Pharmacology Biochemistry and Behavior, vol. 54, No. 1, 1996, pp. 21-30.
International Search Report and Written Opinion for PCT/EP2014/055843 dated Apr. 29, 2014.
International Search Report and Written Opinion for PCT/EP2014/059525 dated Aug. 1, 20154.
Jaggy et al., "Idiopathic epilepsy in 125 dogs: a long-term study. Clinical and electroencephalographic findings". Journal of Small Animal Practice, vol. 39, No. 1, 1998, pp. 23-29.
Loescher et al., "Critical review of current animal models of seizures and epilepsy used in the discovery and development of new antiepileptic drugs". Seizure, vol. 20, 2011, pp. 359-368.

(Continued)

*Primary Examiner* — Sahar Javanmard
(74) *Attorney, Agent, or Firm* — Marc Began; Wendy M. Gombert (57) ABSTRACT

The present invention relates to the use of 1-(4-chlorophenyl)-4-(4-morpholinyl)-2.5-dihydro-1H-imidazol-2-one or a physiologically acceptable salt thereof in a method for treatment and/or prevention of one or more epileptic disorders in a feline animal, preferably a cat.

14 Claims, 4 Drawing Sheets

(56) References Cited

OTHER PUBLICATIONS

Loescher et al., "Evaluation of Epileptic Dogs as an Animal Model of Human Epilepsy". Drug Research, vol. 35, No. 1, 1985, pp. 82-87.

Loescher et al., "The novel antiepileptic drug imepitoin compares favourably to other GABA-mimetic drugs in a seizure threshold model in mice and dogs". Pharmacological Research, vol. 77, 2013, pp. 39-46.

Pakozdy et al., "Epilepsy in Cats: Theory and Practice". Journal of Veterinary Internal Medicine, vol. 28, No. 2, 2014, pp. 255-263.

Podell et al., "Epilepsy and Seizure Classification: A Lesson from Leonardo". Journal of Veterinary Internal Medicine, vol. 13, 1999, pp. 3-4.

Podell et al., "Seizures in Dogs". The Veterinary Clinics of North America, vol. 26, No. 4, Jul. 1996, pp. 779-809.

Rodgers et al., "Animal models of anxiety: an ethological perspective". Brazilian Journal of Medical and Biological Research, vol. 30, 1997, pp. 289-304.

Ross et al., "Developmental and genetic audiogenic seizure models: behavior and biological substrates". Neuroscience and Biobehavorial Reviews, vol. 24, 2000, pp. 639-653.

Rostock et al., "AWD-131-138 as anxiolytic anticonvulsant"., Drugs of the Future, vol. 23, No. 3, 1998, pp. 253-255.

Rostock et al., "D-23129: a new anticonvulsant with a broad spectrum activity in animal models of epileptic seizures". Epilepsy Research, vol. 23, 1996, pp. 211-223.

Rundfeldt et al., "The Pharmacology of Imepitoin: The First Partial Benzodiazepine Receptor Agonist Developed for the Treatment of Epilepsy". CNS Drugs, vol. 28, No. 1, 2014, pp. 29-43.

Schicht et al., "Pharmacokinetics of oxcarbazepine in the dog". Journal of Veterinary Pharmacology and Therapeutics, vol. 19, 1996, pp. 27-31.

Schwartz-Porsche et al., "Therapeutic efficacy of phenobarbital and primidone in canine epilepsy: a comparison". Journal of Veterinary Pharmacology and Therapeutics, vol. 8, 1985, pp. 113-119.

Segan, Scott, "Absence Seizures". Medscape Reference: Drugs, Diseases & Procedures [accessed at http://reference.medscape.com/article/1183858-overview on Apr. 23, 2015], Originally Accessed Aug. 17, 2008, Updated Mar. 28, 2013, pp. 1-9.

Shekhar et al., "Summary of a National Institute of Mental Health workshop: developing animal models of anxiety disorder". Psychopharmacology, vol. 157, 2001, pp. 327-339.

Skradski et al., "A Novel Gene Causing a Mendelian Audiogenic Mouse Epilepsy". Neuron, vol. 31, Aug. 2001, pp. 537-544.

Stables et al., "Progress report on new antiepileptic drugs: A summary of the Second Eilat Conference". Epilepsy Research, vol. 22, 1995, pp. 235-246.

Steimer, Thierry, "Animal models of anxiety disorders in rats and mice: some conceptual issues". Dialogues in Clinical Neuroscience, vol. 13, No. 4, Dec. 2011, pp. 495-506.

Thomas, William B.., "Idiopathic Epilepsy in Dogs". Veterinary Clinics of North America: Small Animal Practice, vol. 30, No. 1, Jan. 2000, pp. 183-206.

Unverferth, et al. "Antiepileptics" Antiepileptics, Wiley-VCH Verlag GmbH & Co. KGaA, Weinheim, 2008, pp. 1-15.

Yarrington et al., "Sequential Neuropathology of Dogs Treated with Vigabatrin, a GABA-Transaminase Inhibitor". Toxicologic Pathology, vol. 21, No. 5, 1993, pp. 480-489.

Sigel et al., "The antiepileptic drug AWD 131-138 stimulates different recombinant isoforms of the GABAA receptor through the benzodiazepine binding site". Neuroscience Letters, vol. 245, No. 2, Apr. 1998, pp. 85-88.

Graham et al. "Pharmacological profile of benzodiazepine site ligands with recombinant GABAA receptor subtypes". European Neuropsychopharmacology, vol. 6, 1996, pp. 119-125.

Lister, Richard G., "Ethologically-Based Animal Models of Anxiety Disorders" Pharmacology and Therapeutics, vol. 16, No. 46, Jan. 1, 1990, pp. 321-340.

Goes et al., "Trait and state anxiety in animal models: Is there correlation?" Neuroscience Letters, vol. 450, 2009, pp. 266-269.

Atack, John R., "The benzodiazepine binding site of GABAA receptors as a target for development of novel anxiolytics." Expert Opinion on Investigational Drugs, vol. 14, No. 5, 2005, pp. 601-618.

Whiting, Paul J., "GABA-A receptors: a viable target for novel anxiolytics?" Current Opinion in Pharmacology, vol. 6, No. 1, Feb. 2006, pp. 24-29.

"Imepitoin", International Nonproprietary Name Search. https://mednet-communities.net/inn/db/ViewINN.aspx?i=8794 [Retrieved on Feb. 26, 2016], 1 page.

Adis Insight, "ELB-139", http://adisinsight.springer.com/drugs/800020261 [Retrieved on Feb. 26, 2016], pp. 1-4.

ClinicalTrials: NTC00322803, ELB139 Given Orally to Patients with Concurrent Panic Disorder, Challenged by CO2 Inhalation AFter a Single Dose and One Week of Treatment, Elbion AG, May 5, 2006. https://clinicaltrials.gov/ct2/show/record/NCT00322803 [Retrieved on Feb. 26, 2016], pp. 1-4.

Atack, John R., "Development of Subtype-Selective GABAA Receptor Compounds for the Treatment of Anxiety, Sleep Disorders and Epilepsy". GABA and Sleep, Molecular, Functional and Clinical Aspects, XXIV, Springer Basel, 2010, pp. 25-72.

* cited by examiner

| Group | Animal No. Sex | Day | Parameter | | | | |
|---|---|---|---|---|---|---|---|
| | | | AST [U/L] | ALT [U/L] | AP [U/L] | GGT [U/L] | GLDH [U/L] |
| 1 | 101 | -1 | 27 | 49 | 34 | <7 | 4 |
| | *male* | 30 | 37 | 67 | 36 | 10 | 3 |
| | 104 | -1 | 25 | 34 | 16 | <7 | 3 |
| | *male* | 30 | 20 | 40 | 17 | <7 | 4 |
| | 105 | -1 | 37 | 49 | 38 | 10 | 4 |
| | *male* | 30 | 21 | 38 | 29 | <7 | <2 |
| | 110 | -1 | 22 | 43 | 18 | <7 | 2 |
| | *female* | 30 | 23 | 41 | 17 | 11 | <2 |
| | 112 | -1 | 18 | 35 | 24 | <7 | <2 |
| | *female* | 30 | 22 | 48 | 24 | <7 | <2 |
| | 113 | -1 | 28 | 38 | 34 | <7 | 4 |
| | *female* | 30 | 28 | 59 | 31 | <7 | 4 |

Figure 2B

| Group | Animal No. Sex | Day | Parameter | | | | |
|---|---|---|---|---|---|---|---|
| | | | AST [U/L] | ALT [U/L] | AP [U/L] | GGT [U/L] | GLDH [U/L] |
| II | 102 | -1 | 21 | 28 | 51 | 10 | 2 |
| | male | 15[1] | 25 | 44 | 42 | <7 | 2 |
| | | 30 | 14 | 28 | 43 | 12 | <2 |
| | 103 | -1 | 28 | 33 | 31 | <7 | 4 |
| | male | 15[1] | 45 | 50 | 26 | <7 | 4 |
| | | 30 | 21 | 35 | 26 | 16 | 2 |
| | 106 | -1 | 21 | 29 | 24 | <7 | <2 |
| | male | 15[1] | 44 | 71 | 20 | 11 | 4 |
| | | 30 | 35 | 55 | 22 | <7 | 3 |
| | 107 | -1 | 26 | 36 | 12 | <7 | 2 |
| | female | 30 | 26 | 43 | 16 | <7 | 3 |
| | 109 | -1 | 31 | 37 | 20 | <7 | <2 |
| | female | 30 | 32 | 52 | 20 | <7 | <2 |
| | 111 | -1 | 24 | 35 | 20 | 12 | 2 |
| | female | 30 | 34 | 80 | 18 | <7 | <2 |

[1] additional examination for individual animals

AST = Aspartate Amonotransferase  GGT = γ-Glutamyl Transferase
ALT = Alanine Aminotransferase  GLDH = Glutamate Dehydrogenase
AP = Alkaline Phosphatase

*Note: Samples with values < 7 (GGT) or < 2 (GLDH) were not measurable (concentration too low). For evaluation, concentrations were set to 3.5 (GGT) or 1 (GLDH).*

FIG. 3

TREATMENT OF EPILEPTIC DISORDERS IN FELINE ANIMALS

FIELD OF THE INVENTION

The present invention relates to veterinary medicine, in particular to the treatment and/or prevention of epileptic disorders in feline animals.

BACKGROUND OF THE INVENTION

Clinical characteristics and treatment with antiepileptic drugs (AEDs) in cats is fundamentally different from dogs and other species. Treatment options are limited, and only limited data are available (Platt 2001). The "International League Against Epilepsy" (ILAE) grades studies for human treatment in four categories of study quality, from class I for well controlled, randomized, double-blind trials with large numbers of cases to class IV for expert opinions and anecdotal case reports. Knowledge on epilepsy treatment in cats can be regarded as lowest grade of evidence (class IV).

Accordingly it is very difficult for a person skilled in the art to choose an appropriate treatment option for cats. In addition, there is a sufficient body of evidence proving that cats react different to most AEDs compared to dogs and other species (Pakozdy et al. 2014). Many AEDs have unfavorable pharmacokinetic properties, low or unproven efficacy or even toxic effects in cats, limiting their potential use as described below in detail.

Oral diazepam has a longer elimination half-life in cats (15-20 h) than in dogs (3-4 h) and cats do not develop functional tolerance to the drug in contrast to other species, including rat, mouse, dog and human. Beside non-fatal adverse events like sedation, polyuria and polydipsia, it has been linked to potentially fatal idiosyncratic hepatotoxicosis, hepatic necrosis and liver failure. Consequently oral diazepam is considered contraindicated in cats (Smith Bailey 2009). This situation is similar to other benzodiazepines, like clorazepate. In terms of efficacy, full benzodiazepine agonists are regarded as very efficacious treatment, but not used due to the possible life-threatening side effects.

Bromide is neither considered sufficiently effective, as seizures are only controlled in about 35% of treated cats, and bromide is associated with severe side effects in cats, especially an idiosyncratic allergic pneumonitis occurring in 35-42% of treated cats. As this adverse event is potentially life-threatening, also bromide is, in contrast to dogs, not a therapeutic option in cats (Boothe et al. 2002).

Phenobarbital is the current treatment of choice, based on its low price, relatively long elimination time, long history of chronic use and acceptable tolerability. However the safety profile and pharmacokinetics are different from dogs and other species. In contrast to dogs, it is not linked to hepatopathy and development of drug tolerance. In cats, sedation, ataxia, polyuria, polydipsia, leukopenia, thrombocytopenia, lymphadenopathies, skin eruptions and coagulopathies have been described as adverse events. In a recent study, sedation was reported in over 40% of all treated cases, and even resulting in two fatal events (one cat was euthanized, as phenobarbital did not control seizures but led to severe sedation, another cat had a fatal accident due to severe sedation) (Pakozdy et al. 2013). In addition, phenobarbital has a strong addictive effect. It is effective in many cases; however there seems to be still a quite high rate of poor responding epileptic cats (ca. 30%).

Approximately half of healthy cats receiving a 20 mg/kg dose of zonisamide experience adverse reactions such as anorexia, diarrhea, vomiting, somnolence and ataxia, and sufficient efficacy has not been convincingly demonstrated.

Levetiracetam was shown in one study to be somewhat effective as add-on therapy in cats with refractory epilepsy under phenobarbital treatment, however in only 10 cats and in a study with methodological weaknesses. Sedation, inappetence and hypersalivation were attributed side-effects. Other drugs were only anecdotally used in cats, and there are no data supporting their routine use in clinical practice (Pakozdy et al. 2014).

Barnes H L et al. (JAVMA 2004, 225(11): 1723-1726) discuss clinical signs, underlying cause, and outcome in 17 cats with seizures.

Fromm G H et al. (Fromm et al. 1985) compared the effect of the experimental antiepileptic gamma-aminobutyric acid (GABA) agonist drug progabide on the trigeminal complex of cats with the effect of established antiepileptic drugs and with the effect of various GABA agonists and antagonists. Their experiments indicated that progabide, but not THIP or muscimol, should have antiepileptic properties. However, the reason for the differential effect of the three GABA agonists remained to be elucidated.

Morimoto K and co-workers (Morimoto K et al. 1993) conducted a comparative study of the anticonvulsant effect of GABA agonists on feline amygdala or hippocampal kindled seizures. They showed that progabide, SKF89976A and gamma-vinyl GABA have potent anticonvulsant effects on partial onset and secondarily generalized limbic seizures. Selective GABAB receptor agonist baclofen, however, did not show anticonvulsant effects on any parameters of kindled seizures.

Quesnel A D et al. (JAVMA 1997, 210(1): 72-77) discuss the clinical management and outcome of cats with seizure disorders in 30 cases.

Schwartz-Porsche D et al. (Feline Epilepsy. In: Inderi R J ed. Problems in Veterinary Medicine. Vol. 1, No. 4, Philadelphia, Pa., Lippincott, 1989: 628-649) gives a review on feline epilepsy.

WO 2013/024023 discloses taste masked pharmaceutical compositions.

In summary, AEDs in cats show an adverse event profile which is significantly different from dogs. Development of drug tolerance, which is common for phenobarbital and benzodiazepines in dogs, humans and rodents, seem to play a minor role in cats. Sedation is a common side effect in all antiepileptic drugs used in the cat, as mentioned above. This can be regarded as relevantly reduced quality of life for the diseased cat, and it also is a disadvantage for the owner-cat interaction.

The objective underlying the present invention is therefore to provide a medication for preventing and/or treating epileptic disorders in feline animals, which overcomes the problems and limitations of the prior art.

DISCLOSURE OF THE INVENTION

Summary of the Invention

In one aspect, the objective of the present invention has surprisingly been solved by providing 1-(4-chlorophenyl)-4-(4-morpholinyl)-2,5-dihydro-1H-imidazol-2-one (imepitoin) or a physiologically acceptable salt thereof for use in a method for treatment and/or prevention of one or more epileptic disorders in a feline animal.

Corresponding methods of prevention and/or treatment of one or more epileptic disorders in a feline animal in need thereof and uses for the preparation of a pharmaceutical composition/medicament for the prevention and/or treatment of one or more epileptic disorders in a feline animal are also intended to be within the scope of the present invention.

Imepitoin (AWD 131-138 or ELB 138; 1-(4-chlorophenyl)-4-(4-morpholinyl)-2,5-dihydro-1H-imidazol-2-one) is a new chemical entity that was presented at the EILAT IV, V and (Imepitoin)

XI conferences on new antiepileptic drugs (AEDs) (Bialer et al., 1999, 2001, 2013).

It was developed in the 1990s from a series of imidazolinones. Furthermore, it was tested in the NINDS-sponsored Anticonvulsant Screening Project (ASP). Imepitoin was selected for further development because of its broad spectrum of anticonvulsant activity, high therapeutic index, and its efficacy in tests predictive for anxiolytic effects. It underwent Phase I clinical studies, but further clinical development for humans was suspended. However, interesting findings in dogs led to the decision to develop imepitoin as a new AED for canine epilepsy. There is a wide range of literature discussing the anticonvulsant efficacy of imepitoin in rodents, dogs and primates (Löscher W et al., 2004; Rieck S et al., 2006; Löscher W et al., 2013; Penderis J et al., 2013; Rundfeldt C et al., 2014; WO 2004/032938).

In another aspect, the objective of the present invention has surprisingly been solved by providing 1-(4-chlorophenyl)-4-(4-morpholinyl)-2,5-dihydro-1H-imidazol-2-one (imepitoin) or a physiologically acceptable salt thereof for the uses as herein described in a method for prevention of one or more epileptic disorders in a feline animal.

In another aspect, the objective of the present invention has surprisingly been solved by providing 1-(4-chlorophenyl)-4-(4-morpholinyl)-2,5-dihydro-1H-imidazol-2-one (imepitoin) or a physiologically acceptable salt thereof for the uses as herein described, wherein the one or more epileptic disorders is selected from the group consisting of: idiopathic (primary, genetic) epilepsy, symptomatic (secondary, structural/metabolic) epilepsy, cryptogenic (of unknown cause, probable symptomatic) epilepsy, reactive epileptic seizures; preferably is idiopathic (primary, genetic) epilepsy and symptomatic (secondary, structural/metabolic) epilepsy and cryptogenic (of unknown cause, probable symptomatic) epilepsy, more preferably is idiopathic (primary, genetic) epilepsy.

In this context and in the course of the present invention, terms "idiopathic epilepsy", "primary epilepsy" and "genetic epilepsy" are used interchangeably. The same holds true for terms "symptomatic epilepsy", "secondary epilepsy" and "structural/metabolic epilepsy", which are also used interchangeably. Finally, terms "probable symptomatic epilepsy", "cryptogenic epilepsy" and "epilepsy of unknown cause" are also used interchangeably.

In yet another aspect, the objective of the present invention has surprisingly been solved by providing 1-(4-chlorophenyl)-4-(4-morpholinyl)-2,5-dihydro-1H-imidazol-2-one or a physiologically acceptable salt thereof for the uses as herein described, wherein 1-(4-chlorophenyl)-4-(4-morpholinyl)-2,5-dihydro-1H-imidazol-2-one or a physiologically acceptable salt thereof is to be administered in combination with one or more further antiepileptic drugs, preferably in form of a simultaneous, a sequential and/or a chronologically staggered co-administration, more preferably in a simultaneous co-administration.

Preferably, such one or more further antiepileptic drug is selected from the group consisting of: phenobarbital, diazepam, potassium bromide, clorazepate, levetiracetam, gabapentin, zonisamide, pregabalin, propentophyllin, taurine, topiramate.

More preferably, the feline animal has first been treated with one or more further antiepileptic drug selected from the group consisting of: phenobarbital, diazepam, potassium bromide, clorazepate, levetiracetam, gabapentin, zonisamide, pregabalin, propentophyllin, taurine, topiramate, preferably with phenobarbital, before the treatment is switched to 1-(4-chlorophenyl)-4-(4-morpholinyl)-2,5-dihydro-1H-imidazol-2-one or a physiologically acceptable salt thereof.

In yet another aspect, the objective of the present invention has surprisingly been solved by providing 1-(4-chlorophenyl)-4-(4-morpholinyl)-2,5-dihydro-1H-imidazol-2-one or a physiologically acceptable salt thereof for the uses as herein described, wherein 1-(4-chlorophenyl)-4-(4-morpholinyl)-2,5-dihydro-1H-imidazol-2-one or a physiologically acceptable salt thereof is to be administered in form of a monotherapy, i.e. not in combination with one or more further antiepileptic drugs, such as the ones disclosed herein, in particular phenobarbital, such as a simultaneous, a sequential and/or a chronologically staggered co-administration.

For the avoidance of doubt, in this context "monotherapy" refers to the treatment with antiepileptic drugs only. That is no other antiepileptic drug is given to the feline animal in the course of such monotherapeutic antiepileptic treatment. However, it may be the case and/or even preferred that one or more other drugs, i.e. non-antiepileptic drugs, are co-administered to the feline animal, e.g. in a simultaneous, a sequential and/or a chronologically staggered co-administration, in order to treat and/or prevent one or more other diseases not being one or more epileptic disorders.

In yet another aspect, the objective of the present invention has surprisingly been solved by providing 1-(4-chlorophenyl)-4-(4-morpholinyl)-2,5-dihydro-1H-imidazol-2-one or a physiologically acceptable salt thereof for the uses as herein described, wherein the one or more epileptic disorders are antiepileptic drug resistant or -refractory epileptic disorders, preferably phenobarbital-resistant or -refractory epileptic disorders, more preferably phenobarbital-resistant or -refractory idiopathic (primary, genetic) epilepsy and phenobarbital-resistant or -refractory symptomatic (secondary, structural/metabolic) epilepsy and phenobarbital-resistant or -refractory probable symptomatic (cryptogenic, of unknown cause) epilepsy, most preferably phenobarbital-resistant or -refractory idiopathic (primary, genetic) epilepsy.

In yet another aspect, the objective of the present invention has surprisingly been solved by providing 1-(4-chlorophenyl)-4-(4-morpholinyl)-2,5-dihydro-1H-imidazol-2-one or a physiologically acceptable salt thereof for the uses as herein described, wherein 1-(4-chlorophenyl)-4-(4-morpholinyl)-2,5-dihydro-1H-imidazol-2-one or a physiologically acceptable salt thereof is to be administered once, twice or three-times daily, preferably once or twice per day, more preferably twice per day.

In yet another aspect, the objective of the present invention has surprisingly been solved by providing 1-(4-chlorophenyl)-4-(4-morpholinyl)-2,5-dihydro-1H-imidazol-2-one or a physiologically acceptable salt thereof for the uses as herein described, wherein 1-(4-chlorophenyl)-4-(4-morpholinyl)-2,5-dihydro-1H-imidazol-2-one or a physiologically acceptable salt thereof is to be administered at a dose of from 1 to 150 mg/kg bodyweight, preferably from 5 to 100 mg/kg bodyweight, more preferably from 5 to 50 mg/kg bodyweight, even more preferably from 20 to 100 mg/kg bodyweight, even more preferably from 20 to 60 mg/kg bodyweight, most preferably 25 to 40 mg/kg bodyweight, and wherein such dose preferably is to be administered once, twice or three-times per day, more preferably once or twice per day, most preferably twice per day.

In yet another aspect, the objective of the present invention has surprisingly been solved by providing 1-(4-chlorophenyl)-4-(4-morpholinyl)-2,5-dihydro-1H-imidazol-2-one or a physiologically acceptable salt thereof for the uses as herein described, wherein the dose to be administered is from 20 to 60 mg/kg bodyweight, preferably from 25 to 40 mg/kg bodyweight, and wherein preferably such dose is to be administered twice per day.

In yet another aspect, the objective of the present invention has surprisingly been solved by providing 1-(4-chlorophenyl)-4-(4-morpholinyl)-2,5-dihydro-1H-imidazol-2-one or a physiologically acceptable salt thereof for the uses as herein described, wherein 1-(4-chlorophenyl)-4-(4-morpholinyl)-2,5-dihydro-1H-imidazol-2-one or a physiologically acceptable salt thereof is to be administered orally or parenterally, preferably orally.

In yet another aspect, the objective of the present invention has surprisingly been solved by providing 1-(4-chlorophenyl)-4-(4-morpholinyl)-2,5-dihydro-1H-imidazol-2-one or a physiologically acceptable salt thereof for the uses as herein described, wherein the feline animal is a cat.

In yet another aspect, the objective of the present invention has surprisingly been solved by providing a pharmaceutical composition comprising 1-(4-chlorophenyl)-4-(4-morpholinyl)-2,5-dihydro-1H-imidazol-2-one or a physiologically acceptable salt thereof for the uses as herein described. In contrast to other feline antiepileptic drug medications, imepitoin advantageously causes no sedation or other considerable side effects in feline animals, even when administered at higher doses, for instance from 20 to 60 mg/kg bodyweight, preferably 25 to 40 mg/kg bodyweight, such as 20 to 60 mg/kg bodyweight, preferably 25 to 40 mg/kg bodyweight once, twice or three-times per day.

Moreover, in view of its mode of action, being a partial agonist at the benzodiazepine binding site, one might expect similar, potentially fatal side effects for imepitoin as for other benzodiazepines. However, surprisingly imepitoin does not cause any toxic effects on liver nor other benzodiazepine-like adverse events.

Furthermore and unexpectedly, imepitoin is highly effective in controlling epileptic seizures in cats. Cats with uncontrolled or continuing seizures under phenobarbital treatment became seizure free after transition to imepitoin monotherapeutic treatment, which is superior to the limited levetiracetam data, where only add-on therapy was effective. This is in strong contrast to the situation in dogs, where imepitoin has only a comparable efficacy to phenobarbital, and is not regarded as a replacement for refractory phenobarbital cases, i.e. patients which suffer from phenobarbital resistant or -refractory epileptic disorders.

In yet another aspect, the objective of the present invention has surprisingly been solved by providing 1-(4-chlorophenyl)-4-(4-morpholinyl)-2,5-dihydro-1H-imidazol-2-one or a physiologically acceptable salt thereof for the uses as herein described, wherein the feline animal has uncontrolled or continuing seizures under treatment with one or more further antiepileptic drug selected from the group consisting of: phenobarbital, diazepam, potassium bromide, clorazepate, levetiracetam, gabapentin, zonisamide, pregabalin, propentophyllin, taurine, topiramate, preferably under treatment with phenobarbital.

In yet another aspect, the objective of the present invention has surprisingly been solved by providing 1-(4-chlorophenyl)-4-(4-morpholinyl)-2,5-dihydro-1H-imidazol-2-one or a physiologically acceptable salt thereof for the uses as herein described, wherein the administration of 1-(4-chlorophenyl)-4-(4-morpholinyl)-2,5-dihydro-1H-imidazol-2-one (imepitoin) or a physiologically acceptable salt thereof leads to complete prevention of seizures (seizure freedom), preferably at doses of 15 mg/kg bodyweight or higher, more preferably at doses of 20 to 60 mg/kg bodyweight, more preferably at doses of 25 to 40 mg/kg bodyweight, even more preferably 15 mg/kg, 20 mg/kg, 25 mg/kg, 30 mg/kg, 35 mg/kg, 40 mg/kg, 45 mg/kg, 50 mg/kg, 55 mg/kg or 60 mg/kg bodyweight, even more preferably 20 mg/kg, 25 mg/kg, 30 mg/kg, 35 mg/kg, 40 mg/kg, 45 mg/kg, 50 mg/kg, 55 mg/kg or 60 mg/kg bodyweight, most preferably 25 mg/kg, 30 mg/kg, 35 mg/kg or 40 mg/kg bodyweight.

In yet another aspect, the objective of the present invention has surprisingly been solved by providing 1-(4-chlorophenyl)-4-(4-morpholinyl)-2,5-dihydro-1H-imidazol-2-one or a physiologically acceptable salt thereof for the uses as herein described, wherein a high initial/starting dose of 1-(4-chlorophenyl)-4-(4-morpholinyl)-2,5-dihydro-1H-imidazol-2-one (imepitoin) or a physiologically acceptable salt thereof is reduced during the course of treatment while maintaining effective control and/or prevention of seizures, preferably moderate or good seizure control, more preferably complete prevention of seizures (seizure freedom). Preferred initial/starting doses are 15 mg/kg bodyweight or higher, more preferably doses of 20 to 60 mg/kg bodyweight, more preferably doses of 25 to 40 mg/kg bodyweight, even more preferably 15 mg/kg, 20 mg/kg, 25 mg/kg, 30 mg/kg, 35 mg/kg, 40 mg/kg, 45 mg/kg, 50 mg/kg, 55 mg/kg or 60 mg/kg bodyweight, even more preferably 20 mg/kg, 25 mg/kg, 30 mg/kg, 35 mg/kg, 40 mg/kg, 45 mg/kg, 50 mg/kg, 55 mg/kg or 60 mg/kg bodyweight, most preferably 25 mg/kg, 30 mg/kg, 35 mg/kg or 40 mg/kg bodyweight. The initial/starting dose can be reduced after initial treatment to lower maintenance doses of 0.5 to 60 mg/kg body weight, preferably from 1 to 30 mg/kg bodyweight, more preferably from 5 to 20 mg/kg bodyweight, even more preferably 1 mg/kg, 2 mg/kg, 5 mg/kg, 8 mg/kg, 10 mg/kg, 12.5 mg/kg, 15 mg/kg, 18 mg/kg, 20 mg/kg, 25 mg/kg or 30 mg/kg bodyweight, most preferably 5 mg/kg, 10 mg/kg, 15 mg/kg or 20 mg/kg bodyweight. Preferably such doses are to be administered once, twice or three-times per day, more preferably once or twice per day, most preferably twice per day. The initial/starting dose should be higher than the lower maintenance dose. The switch from the initial/starting dose (initial treatment) to the lower maintenance dose can be performed at any time of treatment starting one day after treatment initiation, preferably between two days and nine months after treatment initiation, more preferably between three days and six months after treatment initiation, most preferably between three days and three months after treatment initiation.

DETAILED DESCRIPTION OF THE INVENTION

Before the embodiments of the present invention are described in further details it shall be noted that as used herein and in the appended claims, the singular forms "a", "an", and "the" include plural reference unless the context clearly dictates otherwise.

Unless defined otherwise, all technical and scientific terms used herein have the same meanings as commonly understood by one of ordinary skill in the art to which this invention belongs. All given ranges and values may vary by 1 to 5% unless indicated otherwise or known otherwise by the person skilled in the art, therefore, the term "about" was usually omitted from the description and claims. Although any methods and materials similar or equivalent to those described herein can be used in the practice or testing of the present invention, the preferred methods, devices, and materials are now described. All publications mentioned herein are incorporated herein by reference for the purpose of describing and disclosing the substances, excipients, carriers, and methodologies as reported in the publications which might be used in connection with the invention. Nothing herein is to be construed as an admission that the invention is not entitled to antedate such disclosure by virtue of prior invention.

In the following, 1-(4-chlorophenyl)-4-(4-morpholinyl)-2,5-dihydro-1H-imidazol-2-one (imepitoin) is also referred to as compound of the (present) invention.

The compound of the invention can, if it has a sufficiently basic group such as, for example, a secondary or tertiary amine, be converted with inorganic and organic acids into salts. The pharmaceutically acceptable salts of the compound of the invention are preferably formed with hydrochloric acid, hydrobromic acid, iodic acid, sulfuric acid, phosphoric acid, methanesulfonic acid, p-toluenesulfonic acid, carbonic acid, formic acid, acetic acid, sulfoacetic acid, trifluoroacetic acid, oxalic acid, malonic acid, maleic acid, succinic acid, tartaric acid, racemic acid, malic acid, embonic acid, mandelic acid, fumaric acid, lactic acid, citric acid, taurocholic acid, glutaric acid, stearic acid, glutamic acid or aspartic acid. The salts which are formed are, inter alia, hydrochlorides, chlorides, hydrobromides, bromides, iodides, sulfates, phosphates, methanesulfonates, tosylates, carbonates, bicarbonates, formates, acetates, sulfoacetates, triflates, oxalates, malonates, maleates, succinates, tartrates, malates, embonates, mandelates, fumarates, lactates, citrates, glutarates, stearates, aspartates and glutamates. The stoichiometry of the salts formed from the compound of the invention may moreover be an integral or non-integral multiple of one.

The compound of the invention can, if it contains a sufficiently acidic group such as, for example, the carboxy, sulfonic acid, phosphoric acid or a phenolic group, be converted with inorganic and organic bases into its physiologically tolerated salts. Examples of suitable inorganic bases are ammonium, sodium hydroxide, potassium hydroxide, calcium hydroxide, and of organic bases are ethanolamine, diethanolamine, triethanolamine, ethylenediamine, t-butylamine, t-octylamine, dehydroabietylamine, cyclohexylamine, dibenzylethylene-diamine and lysine. The stoichiometry of the salts formed from the compound of the invention can moreover be an integral or non-integral multiple of one.

It is likewise possible for the compound of the invention to be in the form of its solvates and, in particular, hydrates which can be obtained for example by crystallization from a solvent or from aqueous solution. It is moreover possible for one, two, three or any number of solvate or water molecules to combine with the compound of the invention to give solvates and hydrates. By the term "solvate" is meant a hydrate, an alcoholate, or other solvate of crystallization.

In the course of the present invention, (antiepileptic) drug resistant or -refractory epileptic disorders, preferably phenobarbital-resistant or -refractory epileptic disorders, refers to failure of adequate trials of one or two tolerated and appropriately chosen and used anti-epileptic drug (AED) schedules (whether as monotherapies or in combination) to achieve sustained therapeutic success (e.g. seizure freedom or significant reduction in seizure frequency).

Feline Animals

Herein, a feline animal is a member of the Felidae family (i.e. a felid). It may thus belong either to the subfamily felinae or the subfamily pantherinae. The term feline animal encompasses the term cat, e.g., a domestic cat. The term domestic cat encompasses the terms *Felis catus* and *Felis silvestris catus*.

Dosage

The dosage regimen for the compound of the present invention according to the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

A physician or veterinarian can determine and prescribe the effective amount of the drug required to prevent, counter, or arrest the progress of the disorder.

In addition, radioisotope labeled compound of the invention (e.g. $^{99m}Tc$) can be used to examine the distribution of the compound of the invention and their potential metabolites in the body.

Based on the currently available scientific data, the dose of the compounds of the invention, when used for the indicated effects, will be in the range of from 0.5 or 1 to 150 mg/kg bodyweight, preferably from 5 to 100 mg/kg bodyweight, more preferably from 5 to 50 mg/kg bodyweight, even more preferably from 20 to 100 mg/kg bodyweight, even more preferably from 20 to 60 mg/kg bodyweight, most preferably 25 to 40 mg/kg bodyweight. Examples of individual doses are 1 mg/kg, 2 mg/kg, 5 mg/kg, 8 mg/kg, 10 mg/kg, 12.5 mg/kg, 15 mg/kg, 18 mg/kg, 20 mg/kg, 22 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg bodyweight, preferably 10 mg/kg, 15 mg/kg, 20 mg/kg, 25 mg/kg, 30 mg/kg, 35 mg/kg, 40 mg/kg, 45 mg/kg, 50 mg/kg, 55 mg/kg or 60 mg/kg bodyweight, more preferably 20 mg/kg, 25 mg/kg, 30 mg/kg, 35 mg/kg, 40 mg/kg, 45 mg/kg, 50 mg/kg, 55 mg/kg or 60 mg/kg bodyweight, most preferably 25 mg/kg, 30 mg/kg, 35 mg/kg or 40 mg/kg bodyweight. These doses are preferably to be administered once, twice or three-times per day, preferably once or twice daily/once or twice per day, more preferably twice per day. Also, if treated two or three times a day, equal or different doses can be administered.

Alternatively, the dosage can be split into/reduced to anywhere in between one dose once in two days up to one dose once in a week. The treatment is advisable in clinically apparent cases, both in acute as well as in chronic settings.

Administration

Suitable forms for administration are for example parenteral or oral administration of the compound of the invention, preferably oral administration.

The compound of the invention can be formulated for instance in a solid, preferably a tablet formulation, or a liquid formulation.

Efficacy

Efficacy is based on the proportion of animals that achieve seizure freedom (complete prevention of seizures) over a given observation period, for example, 1 week, 2 weeks, 3 weeks, 4 weeks, 1 months, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 1 year, 2 years, 3 years, 4 years, 5 years, 6 years, 7 years, 8 years, 9 years, 10 years or even longer. Such seizure freedom can be achieved, preferably without considerable adverse events, at doses of for example 15 mg/kg bodyweight or higher, such as doses of 20 to 60 mg/kg bodyweight or doses of 25 to 40 mg/kg bodyweight, for instance 15 mg/kg, 20 mg/kg, 25 mg/kg, 30 mg/kg, 35 mg/kg, 40 mg/kg, 45 mg/kg, 50 mg/kg, 55 mg/kg or 60 mg/kg bodyweight, preferably 20 mg/kg, 25 mg/kg, 30 mg/kg, 35 mg/kg, 40 mg/kg, 45 mg/kg, 50 mg/kg, 55 mg/kg or 60 mg/kg bodyweight, more preferably 25 mg/kg, 30 mg/kg, 35 mg/kg or 40 mg/kg bodyweight of the compound of the invention.

During the course of treatment, the initial/starting dose can be reduced to lower maintenance doses to achieve the indicated herein described effects. These lower maintenance doses are preferably in the range of from 0.5 to 60 mg/kg bodyweight, more preferably from 1 to 30 mg/kg bodyweight, even more preferably from 5 to 20 mg/kg bodyweight. Examples of individual doses are 1 mg/kg, 2 mg/kg, 5 mg/kg, 8 mg/kg, 10 mg/kg, 12.5 mg/kg, 15 mg/kg, 18 mg/kg, 20 mg/kg, 22 mg/kg, 25 mg/kg, 30 mg/kg bodyweight, most preferably 5 mg/kg, 10 mg/kg, 15 mg/kg, 20 mg/kg or 25 mg/kg bodyweight. These doses are also preferably to be administered once, twice or three-times per day, preferably once or twice daily/once or twice per day, more preferably twice per day.

In this context and in the context of the present invention "seizure freedom" (complete prevention of seizures) or "seizure-free" means that a given animal does not show one or more seizures in the respective observation period, preferably in a year.

In the context of the present invention "good seizure control" or "good control of seizures" means that a given animal does only show 1 to 5 seizures in the respective observation period, preferably in a year.

In the context of the present invention "moderate seizure control" or "moderate control of seizures" means that a given animal does only show 6 to 10 seizures in the respective observation period, preferably in a year.

In the context of the present invention "poor seizure control" or "poor control of seizures" means that a given animal does only show more than 10 seizures in the respective observation period, preferably in a year.

Considerable Adverse Events

The compound of the invention upon administration of the herein described doses and dosage regimens to a feline animal advantageously and preferably does not cause/elicit considerable adverse events. In this context and in the context of the present invention "considerable adverse events" refers to severe sedation, severe and long lasting somnolence (i.e. longer than 3 hours), hepatotoxicosis, hepatic necrosis, liver failure, kidney damage, kidney failure, drug addiction, leukopenia, thrombocytopenia, lymphadenopathies, coagulopathies and/or death.

BRIEF DESCRIPTION OF THE FIGURES

FIGS. 2A and 2B Results of clinical chemistry for enzymes in blood, routinely used to judge liver function and diagnose liver pathologies (FIG. 2A=untreated/control; FIG. 2 B=imepitoin at 30 mg/kg bodyweight twice daily).

EXAMPLES

The following examples serve to further illustrate the present invention; but the same should not be construed as a limitation of the scope of the invention disclosed herein.

Example 1—Pharmacokinetics

When administered orally at a preferred dose of e.g. 30 mg/kg bodyweight twice daily (60 mg/kg bodyweight daily dose) imepitoin the highest plasma concentration ($t_{Max}$) is reached in median 1 hour (range 0.5 to 3 hours) after administration, in most cases 1 hour. This plasma concentration rapidly declines over the next 24 hours, with a half-life time $t_{1/2}$ of 1.5 hours.

The highest $C_{max}$-values of imepitoin is observed at the first day of dosing (Day 0), 1 to 3 hours after the first dose is given. Mean $C_{max}$ values are 7050 ng/mL for males (n=3) and 6643 ng/mL for females (n=3). Corresponding $AUC_{0-6h}$-values are 28001 ng·h/mL and 24467 ng·h/mL, respectively. After 14 and 29 days of twice daily dosing, a slightly lower exposure of imepitoin is observed compared to the first dosing day, indicating that no accumulation occurs upon long-term BID dosing.

The last measurable concentration is found after more than 18 hours indicating that a dosing interval of 12 hours (twice daily) is adequate to assure permanent plasma levels throughout a chronic treatment.

Figure 1:
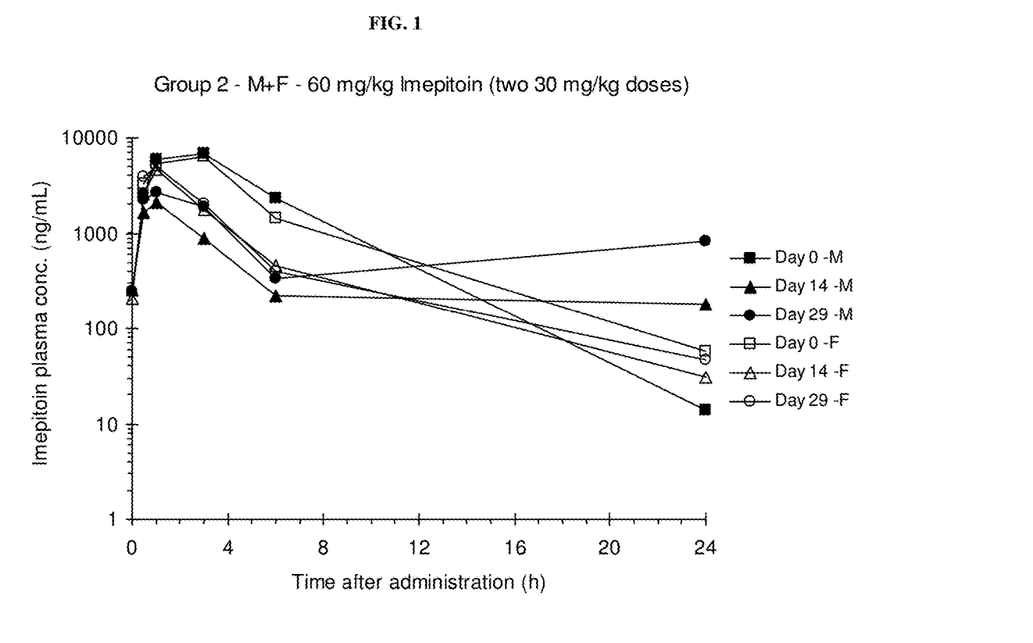
FIG. 1 Mean plasma concentration-time curves of imepitoin after the first oral dose of 30 mg/kg imepitoin in male (M) and female cats (F) at Day 0, Day 14 and Day 29 (semi-logarithmic scale).

The imepitoin serum plasma concentration over time is shown in FIG. 1.

In conclusion, the pharmacokinetic data show a favorable profile for administration in a feline animal.

Example 2—Safety 1

In a randomized, controlled, blinded study the tolerance of imepitoin is investigated in clinically healthy male and female cats after repeated oral administration for 30 days.

Twelve 1-3 years old, male and female domestic short hair cats with a body weight range of 2.8-4.4 kg are assigned to this study. The animals are randomly allocated to two groups, three male and three female animals per group. The test article (imepitoin) is orally administered to the animals of group II at a target dose of 30 mg imepitoin/kg bodyweight twice daily at an interval of 8-12 h on days 0-29. Group I is left untreated serving as controls.

Mortality is not observed. No evidence of a clear effect of the repeated administration of imepitoin to cats on body weight development, food and water consumption, heart rate, respiratory rate and on parameters of laboratory investigations (i.e. hematology, clinical chemistry and urinalysis) is found. No sedation is observed in any animal.

Figure 2A:
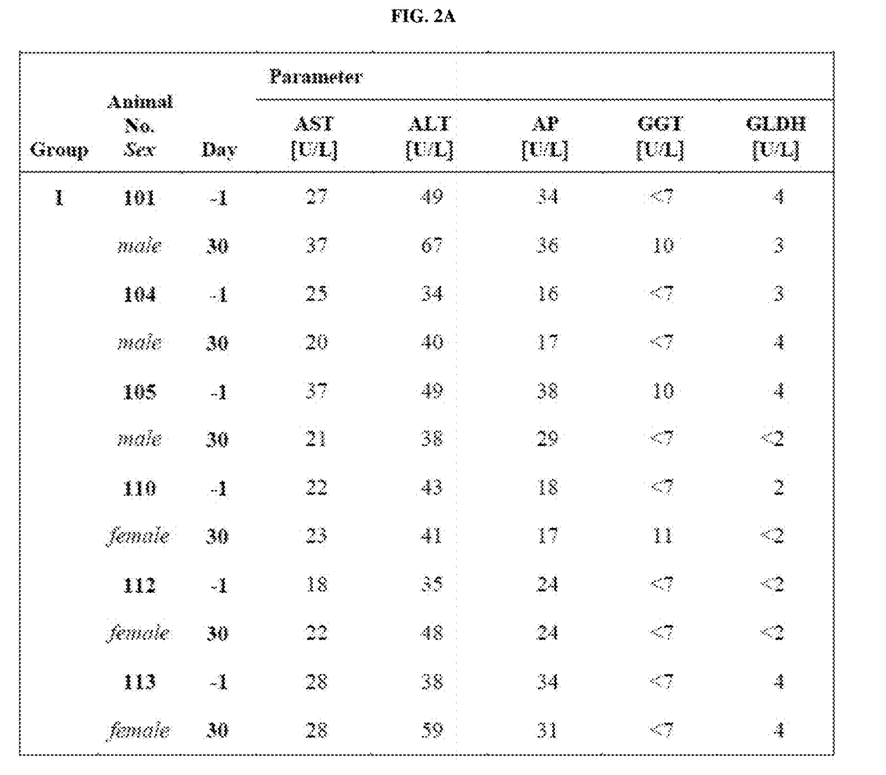
Figure 2B:
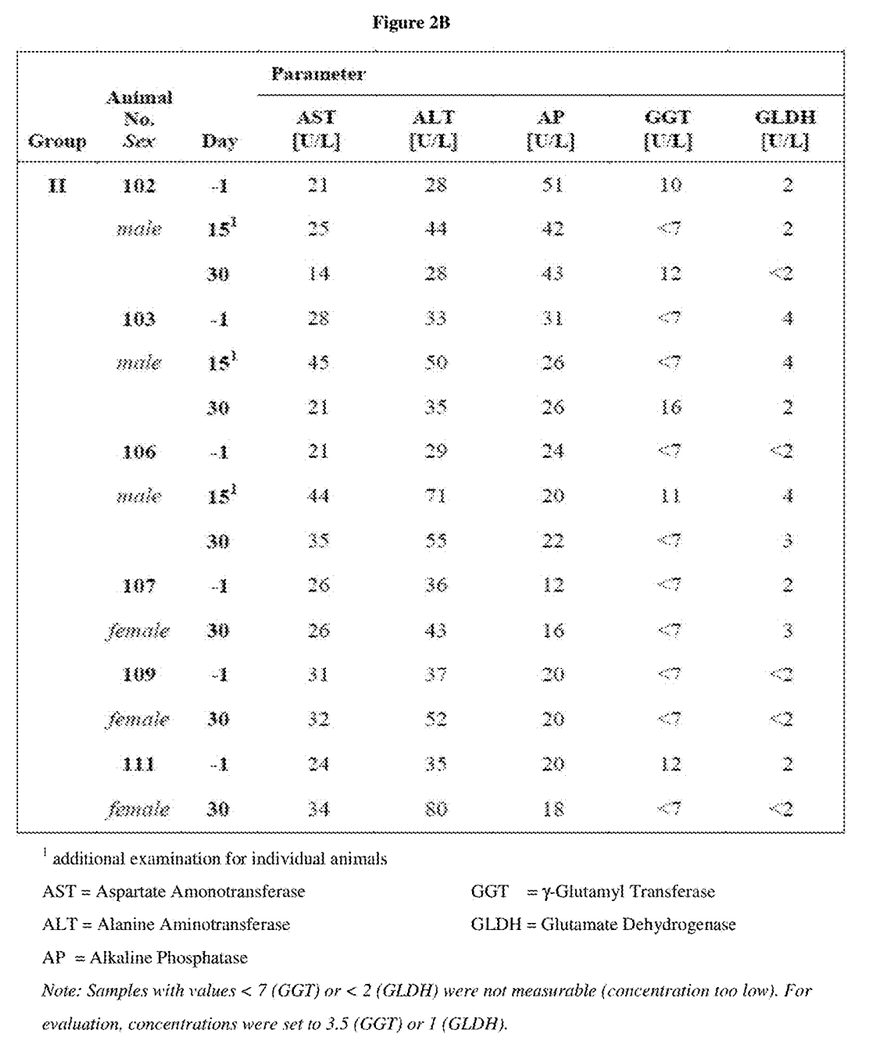

With respect to the liver there is no difference between imepitoin-treated and untreated (control) animals as shown by liver enzyme measurements (FIGS. 2A+2B).

Temporary vomitus or choking is noted in 3 of 6 animals of the treated group from the second week of treatment onwards. Two males of the untreated control group also show a vomitus at one occasion. It is noteworthy that vomitus is observed in cats from time to time after oral administration irrespective of the administered substance.

In conclusion, imepitoin shows a favorable safety profile in feline animals at preferred high doses.

Example 3—Safety 2

Eighteen 9 months old, male and female domestic short hair cats with a body weight range of 2.3-4.9 kg are assigned to this study. The animals are allocated to three test groups employing a pseudo-random body weight stratification procedure that yielded groups with approximately equal mean body weight, with three male and three female animals per group. The test article (imepitoin) is orally administered to the animals at a target dose of 40 mg imepitoin/kg bodyweight and 80 mg imepitoin/kg bodyweight twice daily at an interval of 8-12 h on days 0-30. The third group receives visually identical placebo tablets, to avoid identification of the Placebo Group.

Physical examination a day before treatment start and on study days 7, 14 and 30 includes body temperature (rectal), ocular system, musculoskeletal system, cardiovascular system, reproductive system, lymphatic system, behavior, nervous system, integumentary system, respiratory system, urinary system and gastro-intestinal system. In addition, blood and urine samples are analyzed before treatment and after 30 days.

Figure 3:
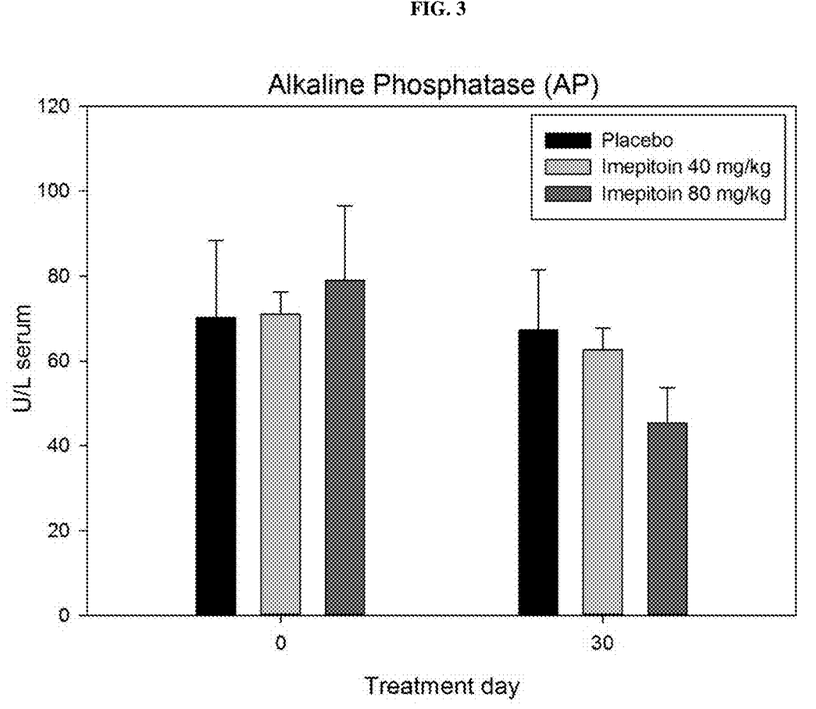
FIG. 3 Measurement of Alkaline Phosphatase (AP) in serum following administration of imepitoin in doses of 40 or 80 mg/kg bodyweight twice daily, or placebo. AP is routinely used to judge liver function and diagnose liver pathologies, and an elevated AP is indicative for a variety of diseases. All values measured here are in the physiological range with normal variance. Day 0 reflects measurement before treatment start.

Repeated oral administration of imepitoin to clinically healthy male and female cats at high doses of 40 and 80 mg imepitoin/kg body weight twice daily for 30 days is well tolerated by all cats, as none of the animals died prematurely and no considerable adverse events are observed. Behavioral changes or sedation is not noted during the course of the study. In this randomized, controlled, blinded study emesis is intermittently observed in the second and third week of treatment, indicating a transient effect at high doses. No hematological or biochemical abnormalities are noted in the blood examination (see e.g. FIG. 3), and urine analysis shows physiological results.

Unexpectedly, imepitoin shows a favorable safety profile in feline animals even at very high doses. In contrast to other antiepileptic drugs, no severe sedation, severe and long lasting somnolence (i.e. longer than 3 hours), hepatotoxicosis, hepatic necrosis, liver failure, kidney damage, kidney failure, drug addiction, leukopenia, thrombocytopenia, lymphadenopathies, coagulopathies and/or death was observed.

Example 4—Efficacy 1

Most other known antiepileptics cause sedation in cats, which is especially with phenobarbital quite pronounced. This is a severe challenge for the human-animal-interaction (pet owner/animal).

Two cats are diagnosed with epilepsy, having severe generalized seizures. Both are treated with imepitoin at a starting dose of 30 mg/kg bodyweight twice daily.

The first cat, a 14 year old European Short-Hair cat, had two severe generalized seizures. Both lasted around two minutes, the cat lost consciousness and was disoriented after the seizure. In addition, a fibrosarcoma and hyperthyroidism was diagnosed. The cat was treated twice a day with 100 mg imepitoin, being a dose of 25 mg/kg bodyweight. It responded immediately to treatment, showing no further seizures. No considerable adverse events were observed. Initially, the cat showed tiredness 1-1.5 hours after application of the drug, which lasted for about two hours. This resolved spontaneously after 10 days of treatment. After three months, the tiredness returned as described above, and consequently the dose was reduced to 20 mg/kg bodyweight, and the tiredness disappeared. Until the end of the observation period of 6 months, the cat did not show any seizures, demonstrating complete seizure freedom for 6 months.

The second cat, 7 years old, experienced two generalized seizures on two consecutive days, and the diagnosis was epilepsy of unknown cause. The cat appeared to be sleepier in the time before occurrence of first seizure. It also responded immediately to treatment with 30 mg/kg bodyweight imepitoin twice a day, but showed the tiredness observed in the first cat already after treatment start. A reduction of the dose to 10 mg/kg bodyweight twice daily resolved the tiredness, but with this dose the cat experienced again a seizure. The dose was increased to 20 mg/kg bodyweight imepitoin twice daily, and the cat showed complete seizure freedom for an observation period of 2.5 months. No tiredness or other adverse events were observed with this last dose.

Surprisingly and in contrast to dogs, a high dose of imepitoin leads to seizure freedom in cats with epilepsy, which is not achieved with low doses. Unexpectedly, no considerable adverse events were observed.

Example 5—Efficacy 2

Compared to untreated status at diagnosis, seizure frequency and severity are significantly reduced—at least 40% of the cats even achieve seizure freedom when administering to feline patients a target dose of e.g. 30 mg imepitoin/kg bodyweight twice daily at an interval of 8-14 hours. Such cats do also not experience considerable adverse events. In most of the other cats, seizure frequency and severity are significantly reduced.

In some animals, treatment with current standard of care, phenobarbital, is not effective and results in frequent severe seizures despite high-dose treatment. Administration of imepitoin in preferred doses, such as 20 to 60 mg/kg bodyweight, preferably such as 25 mg/kg bodyweight to 50 mg/kg bodyweight, more preferably such as 25 mg/kg bodyweight to 40 mg/kg bodyweight, two- or three-times daily reduces seizure frequency and/or severity significantly, in best case until complete seizure freedom.

Example 6—Efficacy 3

Two groups of cats with epileptic disorders are treated with either imepitoin at a preferred dose of 30 mg/kg bodyweight twice daily or with phenobarbital at a common dose of 3.5 mg/kg bodyweight twice daily. In the phenobarbital group, 65% of treated cats experience at least one adverse event, and approximately 40% of all treated cats experience sedation as side effect. In contrast, the occurrence of adverse events is greatly and significantly reduced in the imepitoin treated groups, where about 30% of all cats experience at least on adverse event.

In the phenobarbital group, 30% of treated cats are considered poorly controlled and in 70% epilepsy was well controlled. For imepitoin, in about 15% of cats treatment is not able to control the disease adequately. In 85% of cats seizures are well controlled, and the majority of them reach seizure freedom.

Example 7—Efficacy 4

Cats with epileptic disorders are treated with increasing doses of phenobarbital, starting from 3 mg/kg bodyweight twice daily up to the maximum tolerated dose. With this treatment protocol, sustained and significant reduction in seizure frequency cannot be obtained, and seizures remain poorly controlled. According to this treatment failure this represents drug-resistant epileptic disorders. The treatment of these cats with drug resistant epilepsy is now changed to imepitoin, provided at high doses as for example 30 mg/kg bodyweight twice daily. The seizure frequency of these cats reduced significantly by at least 50% in most cases.

REFERENCES (1) Barnes H L et al., JAVMA 2004, 225(11): 1723-1726
(2) Bialer M et al., Epilepsy Research 1999, 34: 1-41
(3) Bialer M et al., Epilepsy Research 2001, 43: 11-58
(4) Bialer M et al., Epilepsy Research 2013, 103: 2-30
(5) Boothe D M et al., JAVMA 2002, 221(8): 1131-1135
(6) Fromm G H et al., Epilepsia 1985, 26(6): 672-681
(7) Löscher W et al., Epilepsia 2004, 45(10): 1228-1239
(8) Löscher W et al., Pharmacological Research 2013, 77: 39-46
(9) Morimoto K et al., Epilepsia 1993, 34(6): 1123-1129
(10) Pakozdy A et al., Journal of Feline Medicine and Surgery 2013, 15(4): 267-273
(11) Pakozdy A et al., J Vet Intern Med 2014, 28(2):255-263
(12) Penderis J et al., Veterinary Record 2013, 173: 323-324
(13) Platt S R, Journal of the American Animal Hospital Association 2001, 37: 515-517
(14) Quesnel A D et al., JAVMA 1997, 210(1): 72-77
(15) Rieck S et al., The Veterinary Journal 2006, 172: 86-95
(16) Rundfeldt C et al., CNS Drugs 2014, 28: 29-43
(17) Schwartz-Porsche D et al., Feline Epilepsy. In: Inderi R J ed. Problems in Veterinary Medicine. Vol. 1, No. 4., Philadelphia, Pa., Lippincott, 1989: 628-649
(18) Smith Bailey K et al., Journal of Feline Medicine and Surgery 2009, 11: 385-394
(19) WO 2004/032938
(20) WO 2013/024023

The invention claimed is:

1. A method for the treatment of one or more epileptic disorders in a feline animal comprising administering to a feline animal suffering from said one or more epileptic disorders a therapeutically effective dose of 1-(4-chlorophenyl)-4-(4-morpholinyl)-2,5-dihydro-1H-imidazol-2-one or a physiologically acceptable salt thereof, wherein the dose to be administered is from 20 to 60 mg/kg bodyweight twice daily for a consecutive daily period of at least 14 days.

2. A method for the prevention for up to twelve months of one or more epileptic disorders in a feline animal comprising administering to a feline animal suffering from said one or more epileptic disorders a therapeutically effective dose of 1-(4-chlorophenyl)-4-(4-morpholinyl)-2,5-dihydro-1H-imidazol-2-one or a physiologically acceptable salt thereof, wherein the dose to be administered is from 20 to 60 mg/kg bodyweight twice daily for a consecutive daily period of at least 14 days.

3. The method of treatment according to claim 1, wherein the one or more epileptic disorders is selected from the group consisting of idiopathic (primary, genetic) epilepsy, symptomatic (secondary, structural/metabolic) epilepsy, probable symptomatic (cryptogenic, of unknown cause) epilepsy, and reactive epileptic seizures.

4. The method of treatment according to claim 1, wherein 1-(4-chlorophenyl)-4-(4-morpholinyl)-2,5-dihydro-1H-imidazol-2-one or a physiologically acceptable salt thereof is administered in combination with one or more further antiepileptic drugs, in form of a simultaneous, a sequential and/or a chronologically staggered co-administration.

5. The method of treatment according to claim 4, wherein the one or more further antiepileptic drug is selected from the group consisting of: phenobarbital, diazepam, potassium bromide, clorazepate, levetiracetam, gabapentin, zonisamide, pregabalin, propentophyllin, taurine, topiramate.

6. The method of treatment according to claim 1, wherein the one or more epileptic disorders are antiepileptic drug resistant or -refractory epileptic disorders.

7. The method of treatment according to claim 1, wherein 1-(4-chlorophenyl)-4-(4-morpholinyl)-2,5-dihydro-1H-imidazol-2-one or a physiologically acceptable salt thereof is administered as a monotherapy.

8. The method of treatment according to claim 1, wherein the dose to be administered is from 25 to 40 mg/kg bodyweight, and the dose is administered twice per day.

9. The method of treatment according to claim 1, wherein 1-(4-chlorophenyl)-4-(4-morpholinyl)-2,5-dihydro-1H-imidazol-2-one or a physiologically acceptable salt thereof is administered orally or parenterally.

10. The method of treatment according to claim 1, wherein the administration of 1-(4-chlorophenyl)-4-(4-morpholinyl)-2,5-dihydro-1H-imidazol-2-one or a physiologically acceptable salt thereof leads to seizure freedom (complete prevention of seizures) in a given observation period of up to 12 months.

11. The method of treatment according to claim 1, wherein the administration of 1-(4-chlorophenyl)-4-(4-morpholinyl)-2,5-dihydro-1H-imidazol-2-one or a physiologically acceptable salt thereof does not lead to considerable adverse events comprising one or more of severe sedation, severe and long lasting somnolence, hepatotoxicosis, hepatic necrosis, liver failure, kidney damage, kidney failure, drug addiction, leukopenia, thrombocytopenia, lymphadenopathies, coagulopathies and death.

12. The method of treatment according to claim 1, wherein the feline animal is a cat.

13. The method of treatment according to claim 1, wherein the one or more epileptic disorders are one or more of idiopathic (primary, genetic) epilepsy, symptomatic (secondary, structural/metabolic) epilepsy, and probable symptomatic (cryptogenic, of unknown cause) epilepsy.

14. The method of treatment according to claim 1, wherein the one or more epileptic disorders are one or more of phenobarbital-resistant or -refractory epileptic disorders, phenobarbital-resistant or -refractory idiopathic (primary, genetic) epilepsy, phenobarbital-resistant or -refractory symptomatic (secondary, structural/metabolic) epilepsy, and phenobarbital-resistant or -refractory probable symptomatic (cryptogenic, of unknown cause) epilepsy.

* * * * *